US009289626B2

(12) United States Patent
Kawrakow et al.

(10) Patent No.: US 9,289,626 B2
(45) Date of Patent: Mar. 22, 2016

(54) SYSTEMS AND METHODS FOR IMPROVED RADIOISOTOPIC DOSE CALCULATION AND DELIVERY

(71) Applicant: ViewRay Incorporated, Oakwood Village, OH (US)

(72) Inventors: Iwan Kawrakow, Sofia (BG); James F. Dempsey, Chagrin Falls, OH (US)

(73) Assignee: ViewRay Incorporated, Oakwood Village, OH (US)

( * ) Notice: Subject to any disclaimer, the term of this patent is extended or adjusted under 35 U.S.C. 154(b) by 78 days.

(21) Appl. No.: 13/801,835

(22) Filed: Mar. 13, 2013

(65) Prior Publication Data

US 2014/0263990 A1    Sep. 18, 2014

(51) Int. Cl.
*G01D 18/00*    (2006.01)
*A61N 5/10*    (2006.01)
(52) U.S. Cl.
CPC ............ *A61N 5/1031* (2013.01); *A61N 5/1075* (2013.01); *A61N 5/1045* (2013.01); *A61N 2005/1034* (2013.01); *A61N 2005/1076* (2013.01)
(58) Field of Classification Search
CPC ................................. A61B 6/583; A61B 6/584
USPC ...................................................... 250/252.1
See application file for complete search history.

(56) References Cited

U.S. PATENT DOCUMENTS

| 6,125,335 | A | 9/2000 | Simon et al. |
|---|---|---|---|
| 7,907,987 | B2 | 3/2011 | Dempsey |
| 8,044,359 | B2 | 10/2011 | Simon |
| 8,190,233 | B2 | 5/2012 | Dempsey |
| 8,321,179 | B2 | 11/2012 | Simon et al. |
| 2007/0084474 | A1* | 4/2007 | Rivard ........................... 128/898 |
| 2010/0322497 | A1 | 12/2010 | Dempsey et al. |
| 2011/0012593 | A1 | 1/2011 | Shvartsman et al. |
| 2011/0121832 | A1 | 5/2011 | Shvartsman et al. |
| 2011/0241684 | A1 | 10/2011 | Dempsey et al. |
| 2012/0076379 | A1 | 3/2012 | Dempsey et al. |
| 2012/0165652 | A1 | 6/2012 | Dempsey |

FOREIGN PATENT DOCUMENTS

WO    WO-2009/075714 A1    6/2009

OTHER PUBLICATIONS du Plessis, F.C.P., et al. "Characterization of megavoltage electron beams delivered through a photon multi-leaf collimator (pMLC)." *Physics in Medicine and Biology*. Institute of Physics Publishing. Briston, GB. vol. 51. No. 8. (Apr. 4, 2006):2113-2129.
International Search Report issued in International Application No. PCT/US2014/020823, mailed May 28, 2014.

(Continued)

*Primary Examiner* — David Porta
*Assistant Examiner* — Edwin Gunberg
(74) *Attorney, Agent, or Firm* — Mintz Levin Cohn Ferris Glovsky and Popeo, P.C.

(57) ABSTRACT

Disclosed herein are methods including calibrating a radiotherapy machine to identify an effective radiation source size of a radiation source contained within the radiotherapy machine, the radiation source having a nominal radiation source size, to improve accuracy of a predicted dose profile for one or more radiation beams from the radiation source to further improve accuracy of radiation dose calculation and treatment delivery.

30 Claims, 11 Drawing Sheets

(56) References Cited

OTHER PUBLICATIONS van de Guijn, J., et al. "A new model for computerized clinical electron beam dosimetry." *Medical Physics*. AIP. New York, NY, U.S. vol. 14. No. 4. (Jul./Aug. 1987):577-584.

Almond et al. "AAPM TG-51 protocol for clinical reference dosimetry of high-energy photon and electron beams". *Medical Physics*. vol. 26. No. 9. (Sep. 1999): 1847-1870. (www.aapm.org/pubs/reports/rpt_67.PDF).

ArcCheck; Sun Nuclear QA and Dosimetry Tools Product Literature. Retrieved Jun. 11, 2013. (www.sunnuclear.com/medPhys/patientqa/arccheck/arccheck.asp).

Dosimetry 3D Scanner; Sun Nuclear QA and Dosimetry Tools Product Literature. Retrieved Jun. 11, 2013. (www.sunnuclear.com/medPhys/dosimetry/3dscanner/3dscanner.asp).

PTW MP3 Water Phantoms; PTW Product Literature. Retrieved Jun. 11, 2013. (www.ptw.de/mp3.html).

PTW Octavius 4D; PTW Product Literature, Retrieved Jun. 11, 2013. (www.ptw.de/octavius_4d.html).

* cited by examiner

SYSTEMS AND METHODS FOR IMPROVED RADIOISOTOPIC DOSE CALCULATION AND DELIVERY

TECHNICAL FIELD

The subject matter described herein relates generally to the field of radiation therapy dose planning and delivery, and more particularly to devices, systems, articles, and methods used to improve the accuracy of radiation therapy treatment planning, dose calculations, and treatment delivery.

BACKGROUND

External beam radiation devices direct radiation into the body from the outside. The beams can be shaped to conform to the size, shape and location of a target site within a patient reducing the likelihood neighboring non-target cells will be damaged. Treatment planning and dose simulations can be performed before the patient is subjected to actual radiation. Errors in treatment planning can occur resulting in differences between simulated planned dose and the actual dose a patient receives.

SUMMARY

In one aspect, disclosed is a method including calibrating a radiotherapy machine to identify an effective radiation source size of a radiation source contained within the radiotherapy machine, the radiation source having a nominal radiation source size, to improve accuracy of a predicted dose profile for one or more radiation beams from the radiation source to further improve accuracy of radiation dose calculation and treatment delivery.

The method can further include measuring in a phantom a measured dose profile exhibited for the one or more radiation beams from the radiation source. Measuring can further include performing an output factor measurement. The source-to-detector distance can be between 85 cm and 125 cm, or 105 cm. Measuring can include performing a relative dose profile measurement to characterize a penumbra width of the one or more radiation beams. The phantom can have a backscatter of 10 cm or greater. A source-to-detector distance can vary. The source-to-detector distance can vary between 85 cm and 125 cm. The source-to-detector distance can be selected from two or more of the group consisting of 85 cm, 95 cm, 105 cm, 115 cm, and 125 cm. The method can further include opening leaves of a multi-leaf collimator (MLC) on the machine to form an aperture having a square field size. The square field size can be 10 cm×10 cm at isocenter plane. The relative dose profile measurements collected can be processed to extract a penumbra beam width between 30% and 70% or between 20% and 80%. The penumbra beam width can be fit with a linear function of the source-to-detector distance resulting in a measured slope parameter. The method can further include opening leaves of the MLC to form an aperture having a square field size of 6 cm×6 cm at isocenter plane.

The leaves of the MLC can be opened to form an aperture having a second square field size that ranges between 1 cm×1 cm and 10 cm×10 cm. The method can further include running one or more a priori simulations to compute the predicted dose profile. The one or more a priori simulations can be a Monte Carlo simulation. The input radiation source size in the one or more simulations can vary. The input radiation source size can vary by +/−10% of the nominal radiation source size. The method can further include running the one or more simulations wherein the input radiation source size ranges between 0.9, 0.95, 1.0, 1.05, and 1.1 times the nominal radiation source size. The method can further include comparing the predicted dose profile to the measured dose profile. The effective radiation source size can be the input radiation source size value providing a best match between the predicted dose profile and the measured dose profile. The method can further include using the effective radiation source size in subsequent treatment planning for a patient. The subsequent treatment planning can include performing one or more a priori simulations for a third field size. The one or more a priori simulations can be a Monte Carlo simulation. The third field size can be less than or equal to 6×6 cm. The third field size can be less than or equal to 4×4 cm.

In an interrelated aspect, disclosed is a method including directing one or more radiation beams from a radiation source contained within a radiotherapy machine towards a phantom through a multileaf collimator aperture having a field size, the radiation source having a nominal size. The method includes obtaining a measured dose profile exhibited in the phantom of the one or more radiation beams. The method includes running one or more a priori simulations to compute a predicted dose profile for the field size, wherein only input radiation source size is varied. The method includes identifying the effective radiation source size as the input radiation source size providing a best match between the measured dose profile and the predicted dose profile. The method includes using the effective radiation source size identified to subsequently plan and calculate a radiation dose to be given to a patient using the radiotherapy machine. The one or more a priori simulations can be a Monte Carlo simulation. In an interrelated aspect, also disclosed is a system configured to perform the methods described herein.

The details of one or more variations of the subject matter described herein are set forth in the accompanying drawings and the description below. Other features and advantages of the subject matter described herein will be apparent from the description and drawings, and from the claims.

DETAILED DESCRIPTION

Described herein are methods and systems to calibrate radiation therapy systems, such as an intensity modulated radiation therapy (IMRT) delivery units, and improve the accuracy of radiation therapy treatment planning, dose calculations, and treatment delivery. The methods described herein can reduce errors in treatment planning and allow for the delivery of a dose of radiation to a patient that more closely mirrors what is planned during the simulation. The methods described herein can provide for better and more accurate treatment delivery. The methods described herein can be valuable particularly for treatment planning and dose delivery to small field sizes, which can show greater errors between what is measured and what is predicted in dose and penumbra curves. It should be appreciated that although the methods and systems can be used to target radiation therapy to tumors and cancerous cells, that the methods and systems described herein can be used for other indications. For example, the methods and systems described herein can be useful for ablative therapies, and other diagnostic, therapeutic and research purposes.

Radiation therapy takes advantage of a difference between proliferation rates of normal tissue cells and tumor cells. Tumor cells tend to divide much more rapidly and more frequently making them more susceptible to the effects of radiation compared to normal cells. Radiation therapy strives to direct a high enough dose to kill all clonogens in a tumor, but not so high that normal tissue cells are unable to repair themselves. Fractionation of the radiation dose, for example by treating patients according to a prolonged schedule of repeated radiation exposures, can improve the therapeutic ratio and the chance that the tumor cells will be killed instead of the neighboring normal cells. Another way to improve the therapeutic ratio is to decrease the amount of the dose that normal tissues receive relative to the tumor by improved targeting using external beam radiation.

External beam radiation devices direct radiation into the body from the outside, clinical Cobalt-60 ($^{60}$Co radioisotope source) therapy units and megavolt (MV) linear accelerators (linacs) being examples of such therapy machines. IMRT is a type of external beam treatment that can conform radiation beams to the size, shape and location of the target. Systems for IMRT delivery are described in U.S. Pat. No. 7,907,987, which is incorporated by reference herein in its entirety.

Figure 1:
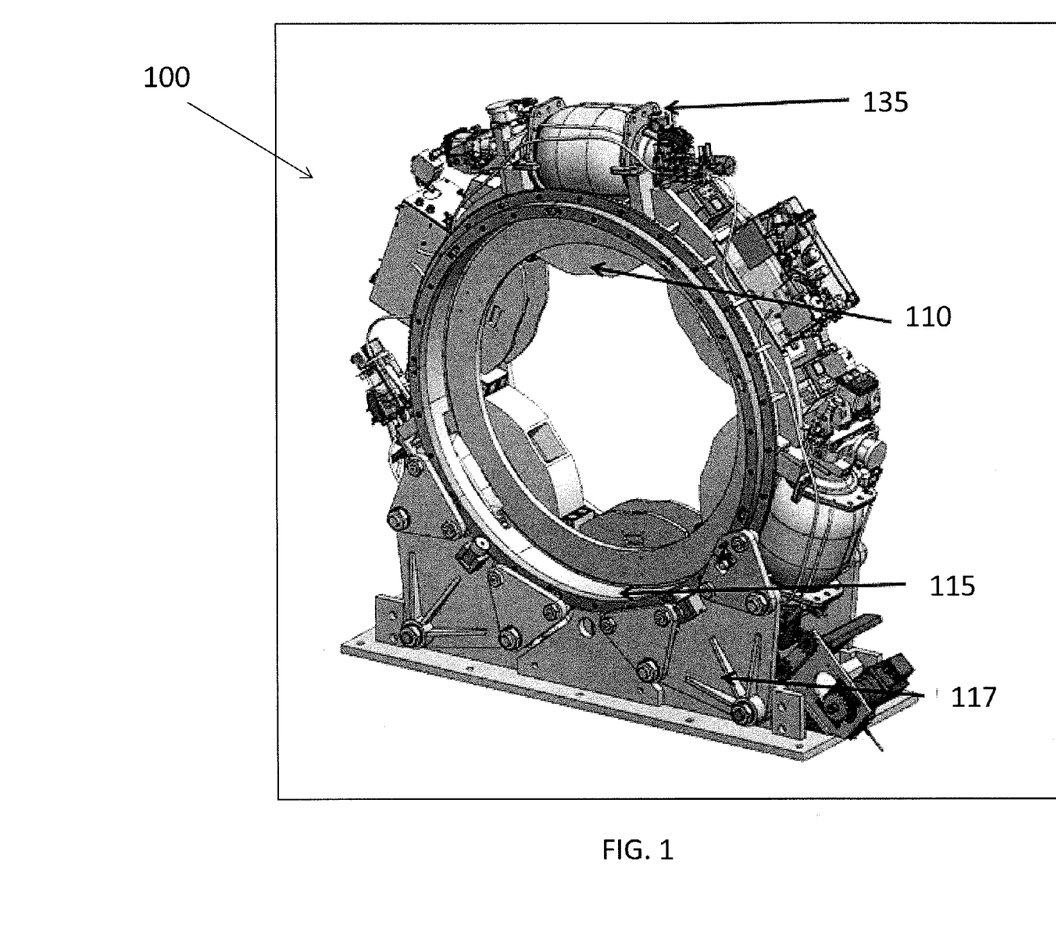
FIG. 1 shows a schematic of a radiation therapy system according to one implementation.
Figure 2:
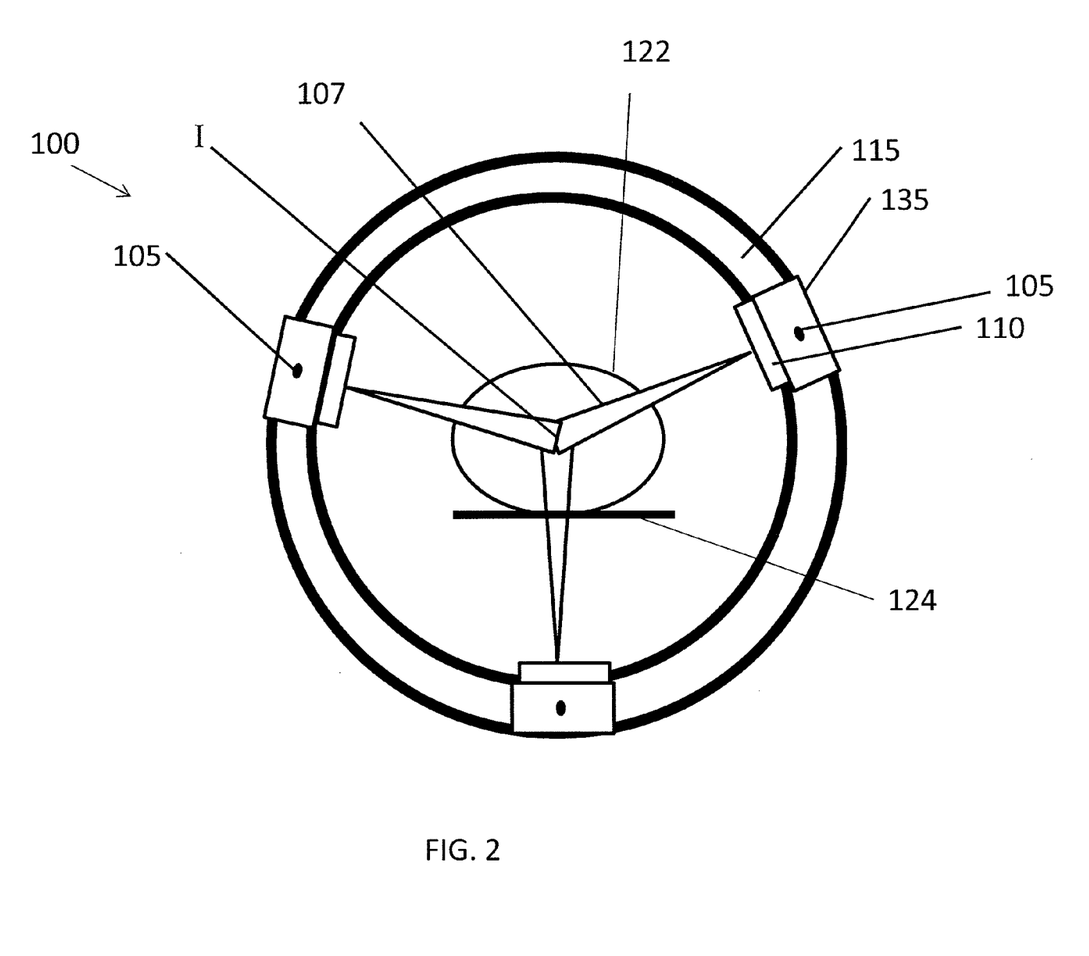
FIG. 2 shows a schematic, cross-sectional view of radiation sources positioned within shielding heads of the radiation therapy system of FIG. 1.

FIGS. 1 and 2 are schematic views of an implementation of an external beam radiation delivery system 100 that permits an operator to administer radiation to a target site within a patient. The system 100 can include multiple radiation sources 105 and multiple multileaf collimators (MLC) 110 positioned on a gantry 115 having a base 117 that can be used for rotating the system 100 around a patient 122 positioned on an adjustable couch 124. Each radiation source 105 can be Cobalt-60 or any other radioisotopic source of radiation that is capable of producing high quality conformal and intensity modulated radiation therapy treatment. Each radiation source 105 can be provided by a supplier as having a nominal size, activity and geometry. Each radiation source 105 can be mounted in a source drawer (not shown) and sealed in a shielding head 135. In some implementations, the system 100 can have three radiation sources 105, each source having a shielding head 135. The shielding heads 135 can be made of tungsten and depleted Uranium encased in 300 series stainless steel. The source drawer can be encased in a shuttle for protection that can move upon low friction bearing or bushing surfaces designed for radiation environments. A head mounting mechanism can be designed to withstand the applicable mechanical structure requirements and can be constructed so that the center of the radiation field for each source 105 can remain within an isocenter, I, to a specified precision, typically sub-millimeter or correctable to the sub-millimeter, throughout range of gantry motion. The design of the head 135 and shuttle can allow the installation of the shuttle drawer in one direction and orientation relative to the head 135 to ensure the proper position and orientation of the source 105.

When in the open position, a portion of the source beam 107 can project through an aperture of the MLC 110 to isocenter I. A source movement control system can have its own position detection system to determine when it is in an open, stand-by, or off state. The open position can be the treatment position with the source 105 exposed, the stand-by position can be a retracted, shielded but not latched position used during the therapy delivery, and off can be a fully retracted and latched position where the shielding level is sufficient to reduce radiation to general population exposure levels. In some implementations, the source output at isocenter I can be 250 cGy/min. The heads 135 can be shielded such that the maximum leakage at the surface of the gantry cover is less than about 2 mR/hr.

Figure 3:
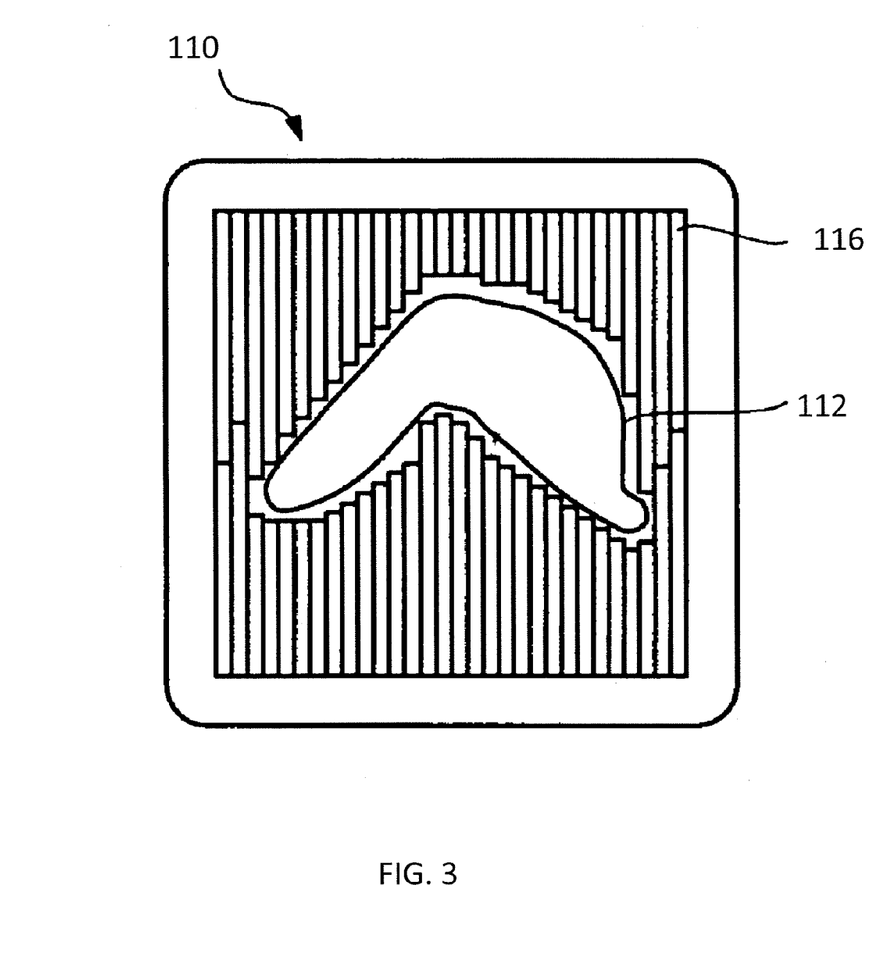
FIG. 3 shows a schematic of a multileaf collimator (MLC) creating an aperture having a field size.

Each shielding head 135 can have a beam shaping multileaf collimator (MLC) 110 (see FIG. 3). The MLC 110 can be positioned adjacent the shielding heads 135. The MLC 110 can have two banks of multiple opposing pairs of leaves 116. The leaves 116 can open to form an aperture 112 of a variety of field sizes. The number of the leaves 116 per bank can vary. The leaves 116 can be made of tungsten or other suitable material or materials. The distance from the radiation source center to the distal side (down-stream side of the leaf) of the MLC 110 can vary, for example, 50 cm or greater. The MLC 110 can employ tongue and groove on the long sides and front face of the MLC leaves 116 to limit interleaf radiation leakage and enable inter-digitations of its leaves 116. Each leaf 116 of each bank can be capable of independent motion. The MLC structure can be supported on a reference surface on the source side with an aluminum frame that then attaches to the gantry 115. There can be pinning locations in the center of the side plate reference surfaces for calibration and alignment to the gantry 115. The leaves 116 can travel parallel to the rotation plane of the radiotherapy unit gantry 115 relative to isocenter I. An MLC control system can control the two opposing banks of leaves 116. The MLC control system can independently position the edge of each leaf 116 to a specified location in order to block a radiation beam and form a field size of a specific shape. Each leaf 116 can be capable of motion which is independent aside from being coordinated with the opposing bank leaf 116 to avoid interference.

Treatment planning of a patient can be performed before the patient is subjected to actual radiation. Treatment planning can use images acquired by 3-D computed tomography (CT), positron emission tomography (PET) and/or magnetic resonance imaging (MRI) in conjunction with computerized dose calculations in order to find out the beam cross section intensity pattern that will best conform the dose to the target shape and location. These diagnostic images can help to determine the precise location of the target cells prior to radiation sessions on the patient. The efficacy of radiation therapy can rely on the accuracy of dose delivery and quality assurance procedures used to detect dosimetric errors. Measurements can be made to verify the accuracy of the delivery of the planned doses calculated by treatment planning systems.

A device called a phantom having known composition and geometry can be used to simulate the in vivo effect the radiation will have on a patient's tissues. Curves of dose-versusdepth within the phantom for a particular beam type can be used to validate dose calculation algorithms employed in planning and simulate what will happen in a patient and can be the basis for radiation treatment planning. Phantoms can be formed of a variety of materials, including but not limited to water, polymers, SOLID WATER, or other tissue-equivalent or mimicking materials, and can have a variety of geometries, anthropomorphic or geometric. Dosimeters can be placed in the phantom at known locations and employed in measuring the ionizing radiation dose to the phantom at points, lines, planes, or volumes inside the phantom. In some implementations of the methods described herein, the dosimeters inside the phantom can be one or more air-filled ionization chambers or an array or matrix of dosimeters. In other implementations, a slab phantom geometry can be used with planar arrays of point dosimeters, 2D film dosimeters, or 3D gel based dosimeters. In some implementations, a 20 cm×20 cm block phantom that houses film and a plurality of MOSFET dosimeters in two or more orthogonal planes can be used. The phantom can be a water phantom having a profile scanning system used with diodes or MOSFETs. The phantom can be a water phantom or a film sandwiched between two slabs of water-equivalent plastic such as SOLID WATER. The phantom can be a polymer plastic cylinder embedded with a cylindrical array of Si diodes (see www.sunnuclear.com/medPhys/patientqa/arccheck/arccheck.asp or www.ptw.de/octavius_4d.html) or a 3D water scanning tank with a robotic detector or detector array (see www.sunnuclear.com/medPhys/dosimetry/3dscanner/3dscanner.asp or www.ptw.de/mp3.html).

Dose simulations can be performed using a priori dose calculation methods such as Monte Carlo simulations or Discrete Ordinates computations using basic physics interaction probabilities to determine the fate of the representative particles. The Monte Carlo simulation can follow the path of individual representative particles through the system and the patient/phantom to determine dose, fluence and other distributions in the patient/phantom. Sufficient representative particles can be transported to produce a statistically acceptable result. For example, several thousand pencil beams or beamlets can be independently targeted to a site with high accuracy. The non-uniform intensity distributions of the individual beamlets can be determined to attain certain specific clinical objectives as determined by an intensity modulated radiation therapy (IMRT) optimization objective function. The Monte Carlo simulation can include detailed knowledge of the geometry and materials of the radiation therapy device and patient and phantom, including the patient or phantom (as characterized by diagnostic imaging, e.g. X-Ray, CT, MRI, PET-CT, etc., and combinations thereof) the therapy targets, critical organs for avoidance or sparing, the source, the shielding housing of the source, the leaves and banks of the MLC, and any other materials in the beam such as the patient couch or MRI coils. Using the Monte Carlo simulation as the dose calculation algorithm for therapy can improve calculation accuracy. Once a treatment plan is generated and quality control checking complete using the simulations, the patient can be immobilized and positioned on the treatment couch. The radiation can be delivered to the patient via the MLC instructions, a process that can be delivered once or repeated daily for many weeks until the prescribed cumulative dose is assumed to be delivered. Leaf sequencing can be used to convert the set of beamlet fluences to an equivalent set of leaf motion instructions or static apertures with associated fluences. The leaves of the MLC shift to form specific patterns, thereby blocking the radiation beams according to the intensity profile from the treatment plan. The characteristics of the exact shapes and delivery of the radiation can also be fully characterized by the Monte Carlo simulation.

Despite improving therapeutic ratio and more accurately delivering radiation therapy to an intended target using beam shaping, imaging, patient immobilization, treatment planning, Monte Carlo simulations, etc. problems can still persist. Problems can occur, for example, the size of the radiation source used in the Monte Carlo simulation can be different from the actual size of the radiation source contained in the machine. Using an inaccurate source size in the simulation algorithm can result in a predicted dose curve that does not match the dose that is actually delivered to the patient. Such errors can increase as the field size decreases and can be higher toward the center of the field where small beams to shape the dose are used and it can matter most. Described herein are methods to determine the effective radiation source size that, in turn, can be used to calibrate the radiation delivery machine for use during subsequent treatment planning. The methods described herein can be used to calibrate the radiation therapy delivery system after radiation source installation to improve the accuracy in the magnitude and shape of the predicted delivered dose profile for the radiation source and thus, improve the accuracy of treatment planning, dose calculations, and treatment delivery.

The terms "nominal source size" or "nominal radiation source size" as used herein generally refer to the size, such as a radius, of the radiation source that is provided by a supplier of the radiation source. The terms "input source size" or "input radiation source size" as used herein generally refer to the radiation source size input to an a priori simulation such as the Monte Carlo algorithm. The terms "effective source size" or "effective radiation source size," "empirical source size" or "empirical radiation source size," can be used interchangeably herein and generally refer to the value of the radiation source size determined using the methods described herein that provides the best match between the measured and predicted dose profiles and that is used for subsequent treatment planning, dose calculation and delivery. It should be appreciated that the effective source size may or may not be equal to the actual radiation source size. The terms "real source size" or "real radiation source size," "actual source size" or "actual radiation source size" as used herein generally refer to the size of the radiation source in reality.

Figure 4:
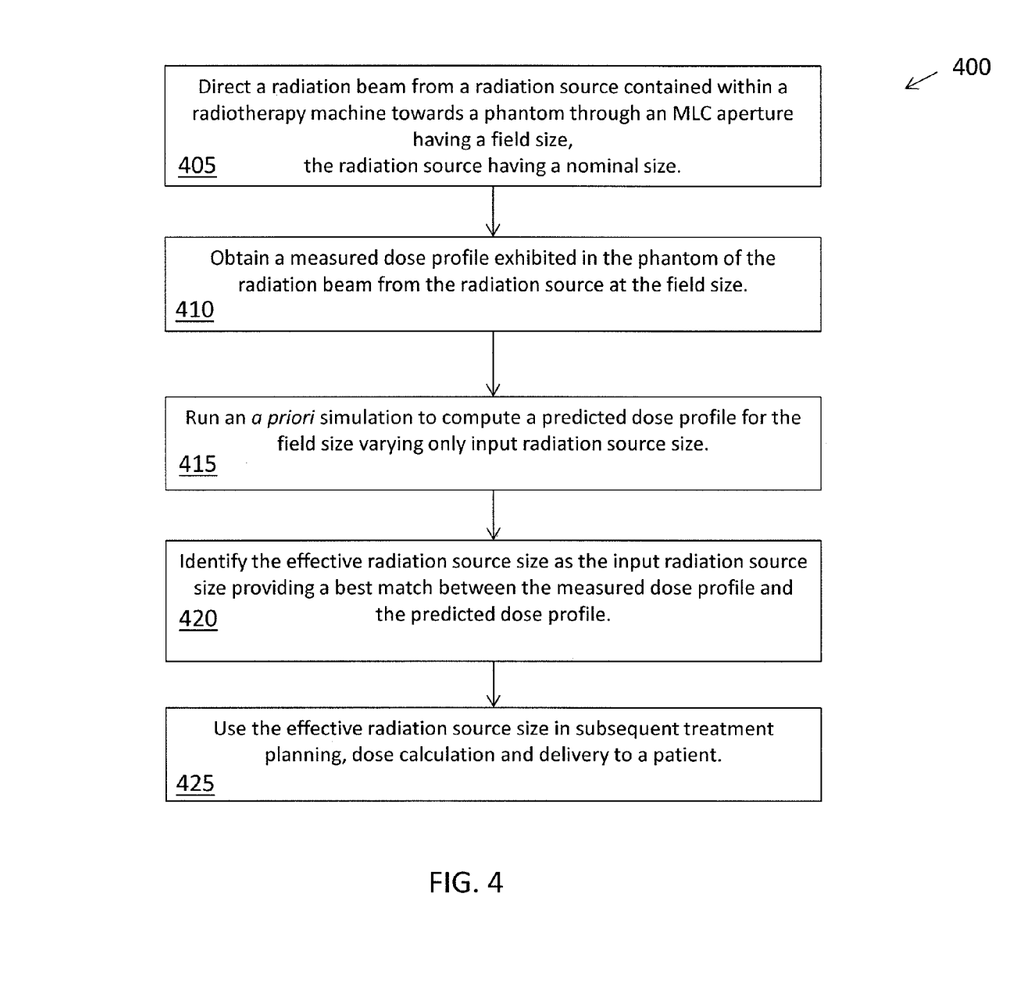
FIG. 4 shows a flow chart of a method for improving accuracy of a radiation dose delivered from a radiation therapy system.

FIG. 4 shows an implementation of a method for improving radiation treatment planning, dose calculation and dose delivery (400). A radiation beam from a radiation source contained within a radiotherapy machine can be directed towards a phantom through an aperture in the MLC leaves set to have a square field size (405). The radiation source can have a nominal source size provided by the supplier. The dose profile exhibited in the phantom can be measured for the field size (410). As will be described in more detail below, two types of measurements can be performed including relative dose profile measurement and output factor measurement. Detector availability can be a factor in selecting the measurement method used. Once the measured dose profile is obtained, an a priori simulation such as a Monte Carlo simulation can be run to compute a predicted dose profile for the field size varying only input radiation source size (415). As will be explained in more detail below, the input radiation source size can be a factor of the nominal radiation source size, such as for example, 0.9, 0.95, 1.0, 1.05, or 1.10 times the nominal size. The input radiation source size providing a best match between the measured dose profile and the predicted dose profile can be identified as the effective source size (420). The effective source size can then be used in subsequent treatment planning, dose calculation and delivery to a patient (425).

"Relative dose profile measurement" as used herein generally refers to a measurement performed, such as on a phantom, to characterize the penumbra width. Such measurements can be performed to verify that the detailed knowledge of the geometry and materials in the Monte Carlo simulation are correct and produce a dose distribution consistent with the measured dose distributions modeled in the phantom dosimeters. The penumbra can be defined herein as the space in the periphery of the main target of radiation therapy receiving between 70% and 30% or between 80% and 20% of maximum dose in a single beam or small beamlet. It is desirable to use a detector having good spatial resolution for this step and a phantom that can accurately position a detector or array of detectors. If measurements are performed in a water phantom with a profile scanning system, diodes or MOSFETS (metal-oxide-semiconductor field-effect transistors) can be used. Alternatively, a film sandwiched between two slabs of (nearly) water-equivalent plastic such as SOLID WATER can be used. In both cases, profile measurements can be performed at a known depth, such as for example 5 cm, in between slabs of solid water equivalent depth behind ion chamber or other detector with a sufficient backscatter (e.g., 5 cm, 10 cm, 20 cm, 30 cm or more) at different source-to-detector distances (SDDs). The number of different SDDs used in the measurements can vary. In some implementations, two, three, four, five or more different SDDs can be used. The SDD can vary as well and can range between about 80 cm and about 130 cm, or between about 85 cm and 125 cm. In some implementations, 5 different SDDs can be used including 85 cm, 95 cm, 105 cm, 115 cm, and 125 cm. In some implementations, leaves of the MLC can be opened to form a 10 cm×10 cm square field at the isocenter plane (see FIGS. 5A and 5B). In other implementations, leaves of the MLC can be opened to form a 6 cm×6 cm square field (see FIGS. 6A and 6B). In other implementations, penumbra width measurements can be employed for more than a single field size, for example both 10 cm×10 cm and 6 cm×6 cm field sizes. Leaves of the MLC can be opened to form square field sizes, including but not limited to, 1 cm×1 cm, 2 cm×2 cm, 3 cm×3 cm, 4 cm×4 cm, 6 cm×6 cm, 7 cm×7 cm, 8 cm×8 cm, 9 cm×9 cm, 11 cm×11 cm, 12 cm×12 cm, 13 cm×13 cm, 14 cm×14 cm, 15 cm×15 cm, or greater cm square fields. The field sizes can vary and can be a function of the configuration of the delivery unit used. For example, the field size can also be multiples of 1.05 cm including, but not limited to, 1.05 cm×1.05 cm, 2.1 cm×2.1 cm, 3.15 cm×3.15 cm, 4.2 cm×4.2 cm, and so on. Measured data can be processed to extract the 30-70% beam penumbra width. The penumbra width determined in this way can be fit with a linear function of SDD, and can result in a measured slope parameter b (i.e., penumbra width=a+b*SDD).

Figure 7:
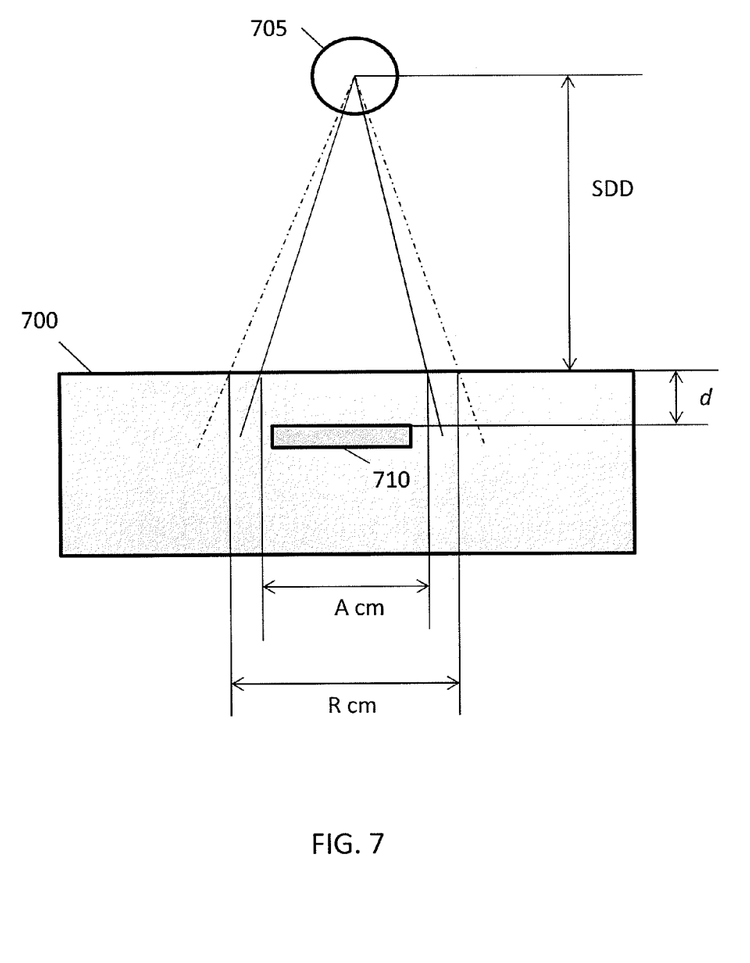
FIG. 7 shows a schematic illustration of a setup for output factor measurement in a phantom.

Output factor (OF) measurements can also be performed. "Output factor" as used herein refers to the ratio of the dose for any field size to the dose for a reference field at the same source-to-surface distance (SDD), and at the same depth in a phantom. The beam output (exposure rate, dose rate in free space, or energy fluence rate) measured in air depends on the field size. As the field size is increased, the output increases because of the increased collimator scatter, which is added to the primary beam. Readings of the output factor measured with an ion chamber having a particular size can be plotted against that field size and values normalized to a reference field. FIG. 7 shows a schematic illustration of a setup for an output factor measurement from a radiation source 705 in a phantom 700. A detector 710 can be located within the phantom 700 positioned at depth d. Dashed lines represent a reference field R and solid lines represent a square field A. SDD is the source-to-detector distance. The phantom can be a slab phantom (as shown in FIG. 7) or a cylindrical phantom normalized to the reference field R.

In some implementations, a reference class chamber at 10 cm depth in a water phantom or in a water-equivalent plastic with sufficient backscatter (e.g. 5 cm, 10 cm, 20 cm, 30 cm or more) can be used. In some implementations, the standard reference field is a square field of 10 cm×10 cm (as set by the AAPM Task Group 51) or 10.5 cm×10.5 cm. The SDD used can range between about 80 cm and about 130 cm, or between about 85 cm and 125 cm. In some implementations, the SDD is 105 cm. In some implementations, the SDD is 85 cm, 95 cm, 105 cm, 115 cm, or 125 cm. Output factor can be measured for a range of square fields including, but not limited to 1 cm×1 cm, 2 cm×2 cm, 4 cm×4 cm, 6 cm×6 cm, 7 cm×7 cm, 8 cm×8 cm, 9 cm×9 cm, 11 cm×11 cm, 12 cm×12 cm, 13 cm×13 cm, 14 cm×14 cm, 15 cm×15 cm or greater cm square fields. TG-51 can be used to convert the chamber reading to absorbed dose to water (see www.aapm.org/pubs/reports/rpt_67.PDF, which is incorporated by reference herein). Alternatively, the chamber readings can be used directly assuming the beam quality change for this measurement set-up is negligible.

Once the measured dose profiles are obtained, an a priori calculation such as a Monte Carlo simulation, can be run to compute predicted dose profiles (415 of FIG. 4). The Monte Carlo simulation can be performed using the known geometry of components such as, for example, the treatment head and MLC geometry, details of metal plates, coil composition and thickness, details of the source container, presence or absence of drawer components. Simulation results in the penumbra region can be quite sensitive to source size and the focal point of the MLC leaves. Known information for all inputs can remain fixed with the exception of the input radiation source size, which is varied. It is unlikely that the source size is off by more than 10% from the nominal radiation source size provided by the supplier. Therefore, simulations can be performed for input radiation source sizes in the range of +/−10% of the nominal radiation source size. In some implementations, the nominal source size is 1 cm radius and the radii of input source for the simulation can be between 0.9 cm and 1.1 cm. It can be sufficient to perform simulations for 5 different input source sizes, for example between 0.9, 0.95, 1.0, 1.05, and 1.1 times the nominal source size radius. It should be appreciated that fewer or more input source sizes can be used in the simulation. Dose profiles and output factors can be computed as described above. The chamber used for OF measurements can be included in the simulations. For example, the Monte Carlo simulation can calculate dose to the sensitive volume of the chamber. The phantom and dosimeter geometry and material can be input in the simulation to increase the accuracy of the result. Dose-to-water or patient may not be the same as dose-to-detector so corrections can be made by simulating the detectors as well. There can be a significant averaging effect for field sizes less than about 4×4 cm.

Figure 5A:
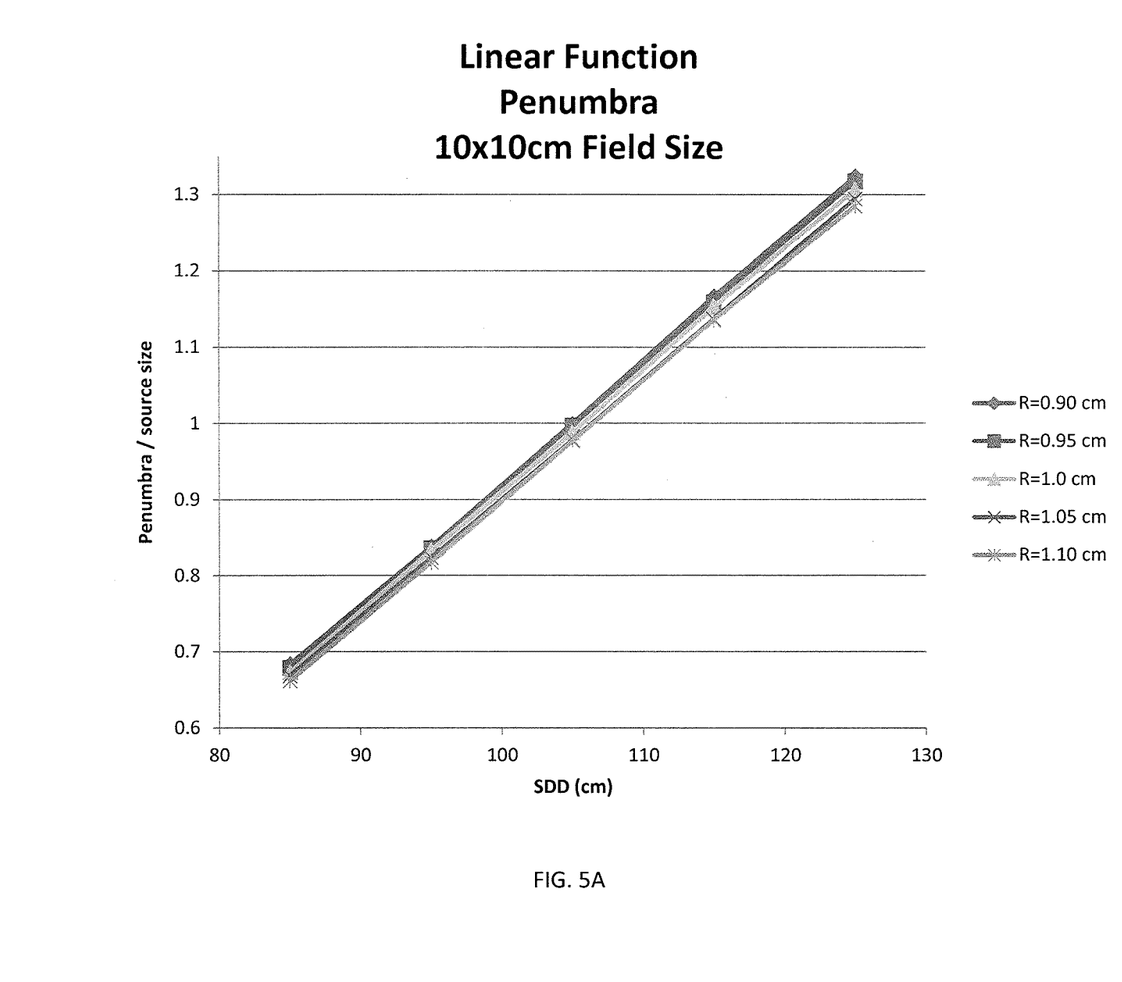
FIG. 5A shows penumbra width as a linear function of source-to-detector distance for a 10 cm×10 cm field size.
Figure 5B:
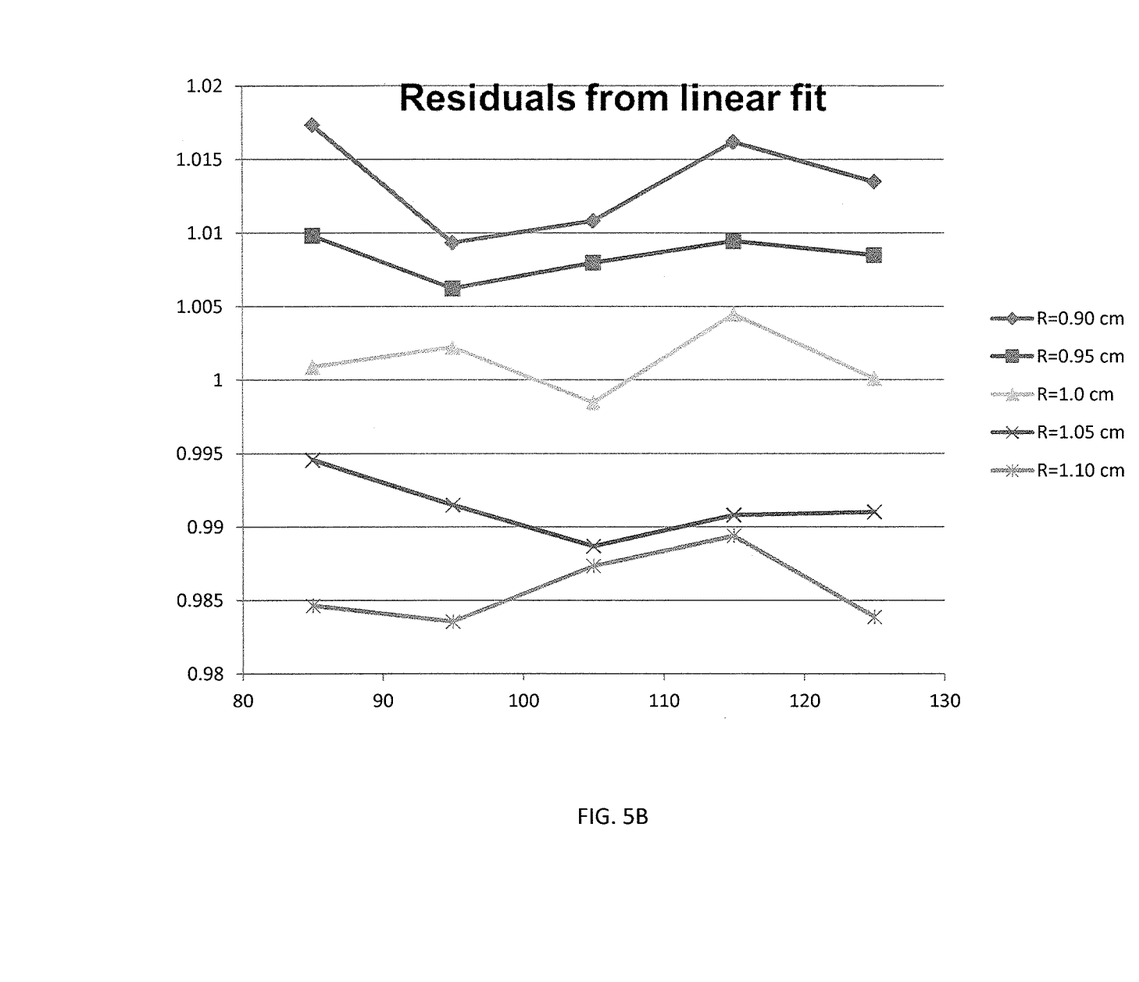
FIG. 5B shows the ratio of the actual penumbra width divided by fit function of FIG. 5A.
Figure 6A:
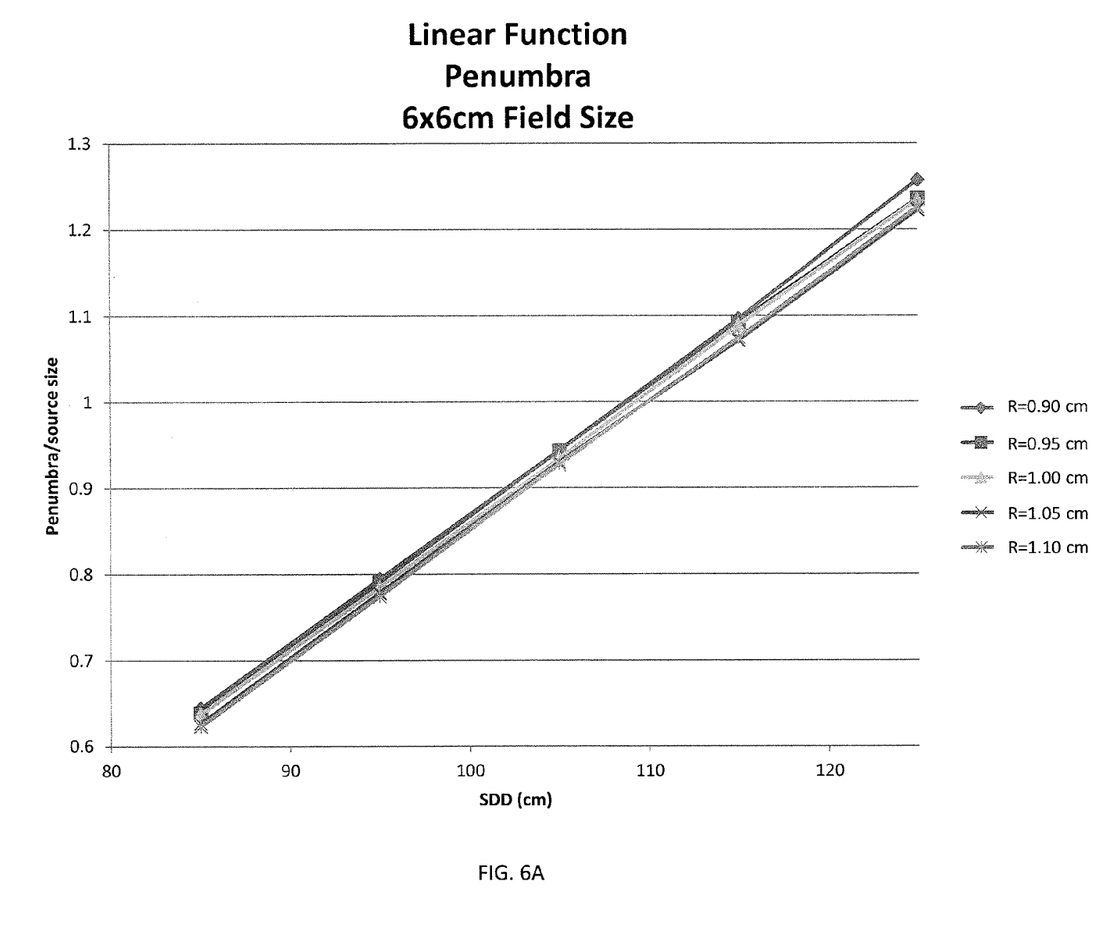
FIG. 6A shows penumbra width as a linear function of source-to-detector distance for a 6 cm×6 cm field size.
Figure 6B:
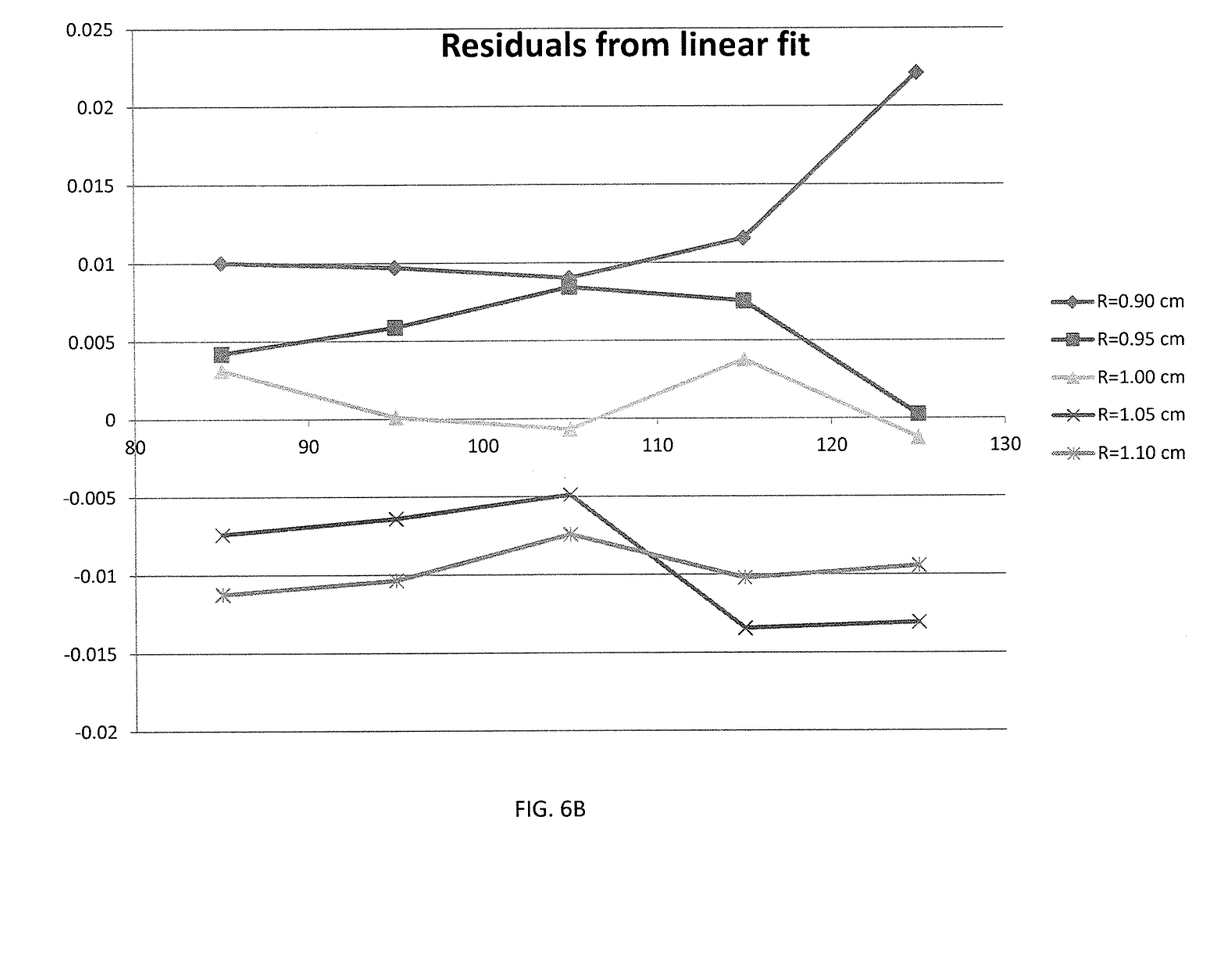
FIG. 6B shows the ratio of the actual penumbra width divided by fit function of FIG. 6A.

The measured dose profile obtained using the phantoms and the predicted dose profile obtained from the simulations can be compared to identify the input radiation source size that provided the best match or the effective radiation source size (420 in FIG. 4). The predicted dose profile data collected as described above can be prepared as follows. The 30-70% penumbra width can be determined for each SDD and each input source size used during the Monte Carlo simulation. The penumbra width can be divided by the input source size. The penumbra width can be fit as a function of SDD with a linear function, i.e., penumbra width divided by source size=a_MC+b_MC*SDD. These steps are illustrated in FIGS. 5A and 5B and FIGS. 6A and 6B. FIGS. 5A and 6A show that penumbra width is indeed a linear function of SDD independent of source size. FIGS. 5B and 6B show the ratio of the actual penumbra divided by the fit function. A small residual dependence on source size can be present, but is generally less than 1.5%. The effective source size can be determined as R=b/b_MC (where b is the measured slope parameter—explained in 410 above).

Figure 8:
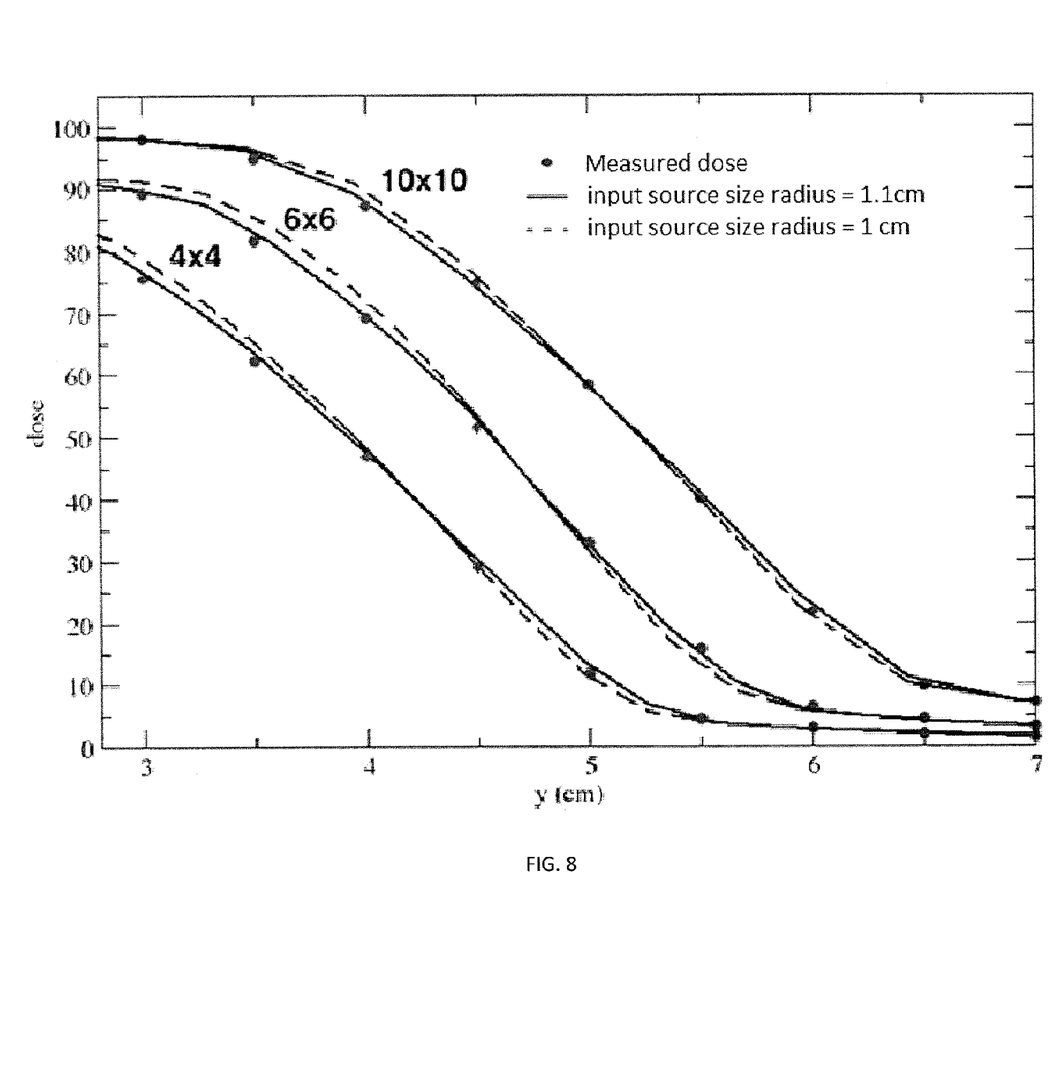
FIG. 8 shows a comparison between measured and predicted dose profiles for various field sizes.

A comparison between measured dose profiles and predicted dose profiles for various square field sizes are shown in FIG. 8. The curves for the dose across leaves for the 4 cm×4 cm, 6 cm×6 cm and 10 cm×10 cm square fields are shifted along the x-axis for easier viewing. The curves of the measured dose profile (dots) for each square field size shows better alignment with the curve of the predicted dose profile in which the input radiation source size was 1.1 cm (solid line curve) than the curve of the predicted dose profile in which the input radiation source size was 1 cm (dashed line curve). The comparison shows that the radiation source size of 1.1 cm has better curve fit than the nominal radiation source size of 1.0 cm stated by the supplier. As such, in this example the effective radiation source size used in treatment planning, dose calculation and delivery to the patient to obtain a more accurate result is 1.1 cm because it was the input radiation source size providing the best match between the predicted and measured dose profiles.

Once the input radiation source size providing the best match between the measured dose profile and the predicted dose profile is identified as the effective source size, the identified effective radiation source size can be used in the subsequent treatment planning, dose calculation and delivery to a patient (425 of FIG. 4). The subsequent steps can include performing Monte Carlo simulations using the effective radiation source size. The field size can be a small field size. In some implementations, the field size can be less than or equal to 6 cm×6 cm. In some implementations, the field size can be less than or equal to 4 cm×4 cm. It should be appreciated that the field size need not be a square field size.

Figure 9:
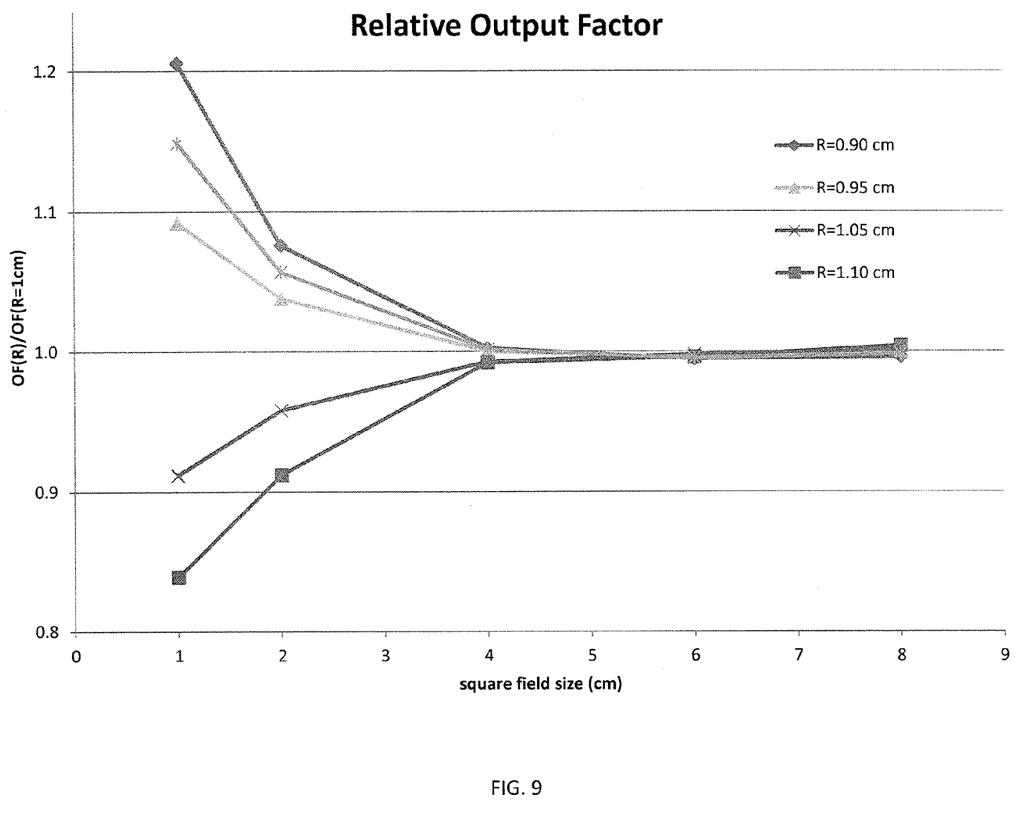
FIG. 9 shows a curve for the measured output factors divided by simulated output factors for a source size at various field sizes.

An alternative method for improving accuracy of a radiation dose delivered from a radiation therapy system can employ the measured and simulated output factors (OFs). A radiation beam from a radiation source contained within a radiotherapy machine can be directed towards a phantom through an aperture in the MLC leaves set to have a square field size. The dose profile exhibited in the phantom for the field size can be measured as an output factor (OF). Once the measured dose profile is obtained, an a priori simulation such as a Monte Carlo simulation can be run to compute a predicted dose profile for the field size varying only input radiation source size. The measured OF can be divided by the simulated OF for the nominal source size for each field size. This can result in a curve as a function of field size. This curve can be plotted together with the simulated OF curves. The effective source size can be extracted by making a fit of the measured curve of the type measured curve=a*simulated curve below +(1−a)*simulated curve above, which then gives for the source radius R=a*Radius (below)+(1−a)*Radius (above). Here, "below" and "above" refer to the Monte Carlo simulated data that bracket the measurement from below and from above. FIG. 9 shows simulations performed for 0.9, 0.95, 1.0, 1.05, and 1.1 cm source sizes and shows a hypothetical measured curve (star curve) and the bracket curves below (triangles) and above (diamonds) are the Monte Carlo computed OF ratios. The OF curves for 0.9, 0.95, 1.05, and 1.1 are divided by the curve for radius 1.0 to make the procedure more robust given OF measurements can vary with field size for small fields.

When comparing measured OF to MC-simulated OF, there can be generally good agreement for field sizes above 6×6 cm. Smaller field sizes, for example less than 4.2×4.2 cm, can be more challenging. For example, 2.1×2.1 field sizes can be sensitive to source details and more difficult to measure reliably. The accuracy of the OF method may suffer from the fact that OFs of small fields are more sensitive to the source radius. The OF of smaller fields can also be influenced by the angle of divergence of the MLC leaves, which may be slightly different (a few percent) from the MLC design specifications. The accuracy of the penumbra method can be limited by the finite detector resolution, the precision of extracting penumbra width from the measured data, and experimental setup inaccuracies. Thus, a practical solution may be that the MC data is generated for a range of leaf-end angles (for each different source size as described above). In this case, one can determine the source size radius by fitting simultaneously penumbra width and OF, a process that can also reveal actual leaf-end inclination. After having determined the source size radius (and potentially leaf-end angle) in this way, the accuracy can be verified by computing profiles and OFs using the just determined source size (and potentially leaf-end angle).

One or more aspects or features of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g., mouse, touch screen, etc.), and at least one output device.

These computer programs, which can also be referred to programs, software, software applications, applications, simulations, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow(s) when depicted in the accompanying figures and/or described herein do not necessarily require the particular order shown, or sequential order, to achieve desirable results. Other implementations may be within the scope of the following claims.

What is claimed is:

1. A method comprising:
    calibrating a radiotherapy machine to identify an effective radiation source size of a radiation source contained within the radiotherapy machine, the radiation source having a nominal radiation source size, to improve accuracy of a predicted dose profile for one or more radiation beams from the radiation source to further improve accuracy of radiation dose calculation and treatment delivery, wherein the effective radiation source size is an input radiation source size providing a best match between a predicted dose profile and a measured dose profile.

2. The method of claim 1, further comprising measuring in a phantom a measured dose profile exhibited for the one or more radiation beams from the radiation source.

3. The method of claim 2, wherein measuring further comprises performing a relative dose profile measurement to characterize a penumbra width of the one or more radiation beams.

4. The method of claim 3, wherein the phantom has a backscatter of 10 cm or greater.

5. The method of claim 4, wherein a source-to-detector distance is varied.

6. The method of claim 5, wherein the source-to-detector distance varies between 85 cm and 125 cm.

7. The method of claim 5, wherein the source-to-detector distance is selected from two or more of the group consisting of 85 cm, 95 cm, 105 cm, 115 cm, and 125 cm.

8. The method of claim 7, further comprising opening leaves of a multi-leaf collimator (MLC) on the machine to form an aperture having a square field size.

9. The method of claim 8, wherein the square field size is 10 cm×10 cm at isocenter plane.

10. The method of claim 9, wherein relative dose profile measurements collected are processed to extract a penumbra beam width between 30% and 70% or between 20% and 80%.

11. The method of claim 10, wherein the penumbra beam width is fit with a linear function of the source-to-detector distance resulting in a measured slope parameter.

12. The method of claim 11, further comprising opening leaves of the MLC to form an aperture having a square field size of 6 cm×6 cm at isocenter plane.

13. The method of claim 2, wherein measuring further comprises performing an output factor measurement.

14. The method of claim 13, wherein a source-to-detector distance is between 85 cm and 125 cm.

15. The method of claim 14, wherein the source-to-detector distance is 105 cm.

16. The method of claim 11, wherein the leaves of the MLC are opened to form an aperture having a second square field size that ranges between 1 cm×1 cm and 10 cm×10 cm.

17. The method of claim 16, further comprising running one or more a priori simulations to compute the predicted dose profile.

18. The method of claim 17, wherein only the input radiation source size in the one or more a prioiri simulations varies.

19. The method of claim 18, wherein the input radiation source size varies by +/−10% of the nominal radiation source size.

20. The method of claim 19, further comprising running the one or more simulations wherein the varying of the input radiation source size includes values that are 0.9, 0.95, 1.0, 1.05, and 1.1 times the nominal radiation source size.

21. The method of claim 20, further comprising comparing the predicted dose profile to the measured dose profile.

22. The method of claim 1, wherein the radiation source is an isotope.

23. The method of claim 1, comprising:
    measuring the measured dose profile, at a phantom, resulting from the treatment delivery by the radiation source, the radiation source having the nominal radiation source size representing an actual size of the radiation source;
    calculating the predicted dose profile based on a simulation, independent of the measured dose profile, the calculating comprising varying the input radiation source size, corresponding to the radiation source, in the simulation to vary the predicted dose profile produced by the simulation to generate a plurality of candidate dose profiles, wherein the varying includes changing a physical dimension of the nominal radiation source size in the simulation;
    identifying, based on the plurality of candidate dose profiles resulting from the varying, and based on the measured dose profile, of the input radiation source size that produces the best match between the measured dose profile and one of the plurality of candidate dose profiles;
    defining the predicted dose profile as the one of the plurality of candidate dose profiles providing the best match; and
    defining the effective radiation source size as the identified input radiation source size.

24. The method of claim 1, further comprising using the effective radiation source size in subsequent treatment planning for a patient.

25. The method of claim 24, wherein the subsequent treatment planning comprises performing one or more a priori simulations for a third field size.

26. The method as in claim 25, wherein the third field size is less than or equal to 6×6 cm.

27. The method as in claim 26, wherein the third field size is less than or equal to 4×4 cm.

28. The method as in claim 17, wherein the one or more a priori simulations is a Monte Carlo simulation.

29. A method comprising:
   directing one or more radiation beams from a radiation source contained within a radiotherapy machine towards a phantom through a multileaf collimator aperture having a field size, the radiation source having a nominal size;
   obtaining a measured dose profile exhibited in the phantom of the one or more radiation beams;
   running one or more a priori simulations to compute a predicted dose profile for the field size, wherein only input radiation source size is varied;
   identifying the effective radiation source size as the input radiation source size providing a best match between the measured dose profile and the predicted dose profile; and
   using the effective radiation source size identified to subsequently plan and calculate a radiation dose to be given to a patient using the radiotherapy machine.

30. The method of claim 29, wherein the one or more a priori simulations is a Monte Carlo simulation.

* * * * *